US00PP09471P

United States Patent [19]

Challet

[11] Patent Number: Plant 9,471

[45] Date of Patent: Mar. 12, 1996

[54] CHRYSANTHEMUM PLANT NAMED 'CHASICA'

[75] Inventor: Jean-Pierre Challet, Lafayette, Calif.

[73] Assignee: Selection New Plant Sarl, Le Cannet des Maures, France

[21] Appl. No.: 274,000

[22] Filed: Jul. 12, 1994

[51] Int. Cl.[6] ..... A01H 5/00

[52] U.S. Cl. ..... Plt./76

[58] Field of Search ..... Plt./76, 79

[56] References Cited

U.S. PATENT DOCUMENTS

| | | | |
|---|---|---|---|
| P.P. 3,194 | 5/1972 | Shoesmith | Plt./79 |
| P.P. 3,218 | 6/1972 | Vogel | Plt./79 |
| P.P. 3,409 | 11/1973 | Jessel, Jr. et al. | Plt./79 |
| P.P. 3,463 | 2/1974 | Shoesmith | Plt./79 |
| P.P. 3,890 | 5/1976 | Jessel, Jr. et al. | Plt./76 |

*Primary Examiner*—Howard J. Locker
*Attorney, Agent, or Firm*—Burns, Doane, Swecker & Mathis

[57] ABSTRACT

A new and distinct Chrysanthemum cultivar named 'Chasica' is provided. The new cultivar was the result of a controlled breeding program. Attractive very large double incurved blossoms of the pompon type are formed that are deep red-bronze on the inside and golden-bronze on the outside. The blossoms are long lasting and the coloration is well maintained with maturity. The response period of the flowers is approximately nine and one-half weeks. Recurrent profuse flower production throughout the year is possible. The plant possesses strong stems, and commonly assumes a height of approximately 45 cm. The new cultivar is particularly suited for use in the production of a decorative pot Chrysanthemum and can be grown single-stem or disbudded. No growth regulator is required to achieve the specified plant height.

2 Drawing Sheets

SUMMARY OF THE INVENTION

The present invention comprises a new and distinct cultivar of Chrysanthemum, botanically known as *Dendranthema grandiflora,* and hereinafter is referred to by the cultivar name 'Chasica'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during October 1987 at Nuaille, Trementines, France. The female parent (i.e., the seed parent) was an unnamed plant designated 80-19-2 (non-patented in the United States) having a large yellow pompom flower that generally was too tall for pot mum production, and the male parent (i.e., the pollen parent was an unnamed plant designated 82-24-7 (non-patented in the United States) having a large double red pompom flower that was bred during 1982 and possessed foliage that could not well tolerate high density growing conditions. The parentage of the new cultivar can be summarized as follows:

80-19-2×82-24-7.

The seeds resulting from the above pollination were sown and many small plantlets were obtained which were physically and biologically different from each other. Selective study resulted in the identification of a single plant of the new variety.

It was found that the new cultivar of the present invention:

(a) exhibits attractive double very large incurved pompon blossoms that are deep red-bronze on the inside and golden-bronze on the outside, (b) exhibits a flower response period of approximately nine and one-half weeks.

(c) forms attractive green foliage, (d) achieves a short plant height, and (e) is particularly suited for pot mum production on a recurrent basis throughout the year.

The new cultivar is intended primarily as the decorative pot Chrysanthemum for growing indoors in a disbudded state with one bloom per stem. However, it also can be grown for cut flower production in those instances where stems of approximately 40 cm. are acceptable. Also, the new cultivar can be grown outdoors at temperatures above freezing.

An increased number of branches readily can be induced by pinching. The pinching of a cutting commonly produces 3 or 4 stems. No growth regulator is required to produce the specified plant height.

The new cultivar can be considered to be an October-flowering greenhouse variety with the natural flowering season commonly occurring in weeks 42 and 43 of the year. Attractive blossoms can be produced on a recurrent basis throughout the year with the indicated nine and one-half week response period. The blossoms are long lasting and commonly can be maintained for approximately 3 to 4 weeks, both on the plant and in a vase.

Asexual reproduction of the new cultivar by cuttings initially taken during 1988, as performed in Nuaille, Trementines, France, in a controlled environment has demonstrated that the characteristics of the new cultivar as herein described are firmly fixed and are retained through successive generations of asexual propagation.

'Chasica' has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the 'Orange Bowl' cultivar (non-patented in the United States), the 'Chasica' cultivar is found to exhibit a faster response period of approximately 9.5 weeks vs. approximately 10 weeks, a greater height, a smaller blossom size, and pointed leaves unlike the 'Orange Bowl' cultivar.

The new cultivar is being marketed under the Cello trademark.

BRIEF DESCRIPTION OF THE PHOTOGRAPHS

The accompanying photographs were prepared during June, 1994, and show as nearly true as it is reasonably possible to make the same in color illustrations of the character, typical and plant parts of the new cultivar of the present invention. The plants were 13 weeks of age and were grown at Nuaille, Trementines, France, under standard greenhouse conditions which approximate those commonly utilized for the production of decorative pot mums. The plant had received one application of Alar growth regulant at a concentration of 3 grams per liter and had been disbudded in order to encourage the formation of one large bloom per stem. Any labels shown in FIG. 3 are 2.5 cm. in width and can be used for size comparisons.

DETAILED DESCRIPTION

Figure 1:
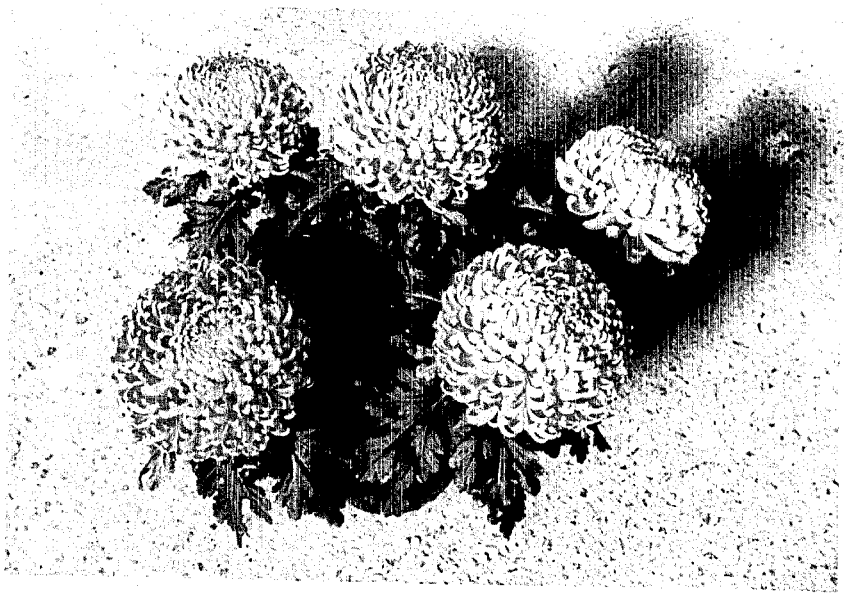
FIG. 1 illustrates typical specimens of the overall plant wherein five cuttings were placed in a 20 cm. pot. The large double incurved flowers that are deep red-bronze on the inside and golden-bronze on the outside, as well as the foliage, are apparent.
Figure 2:
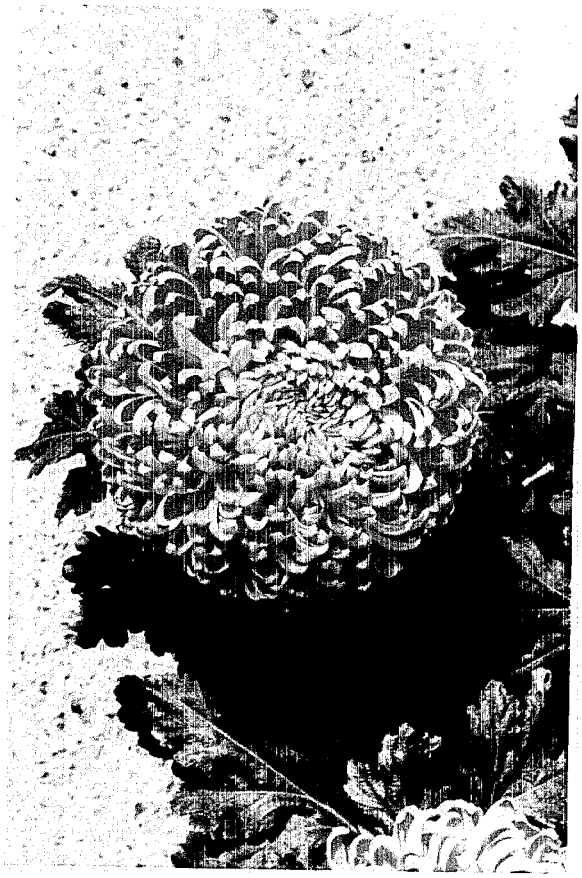
FIG. 2 illustrates a closer view of a typical incurved flower.
Figure 3:
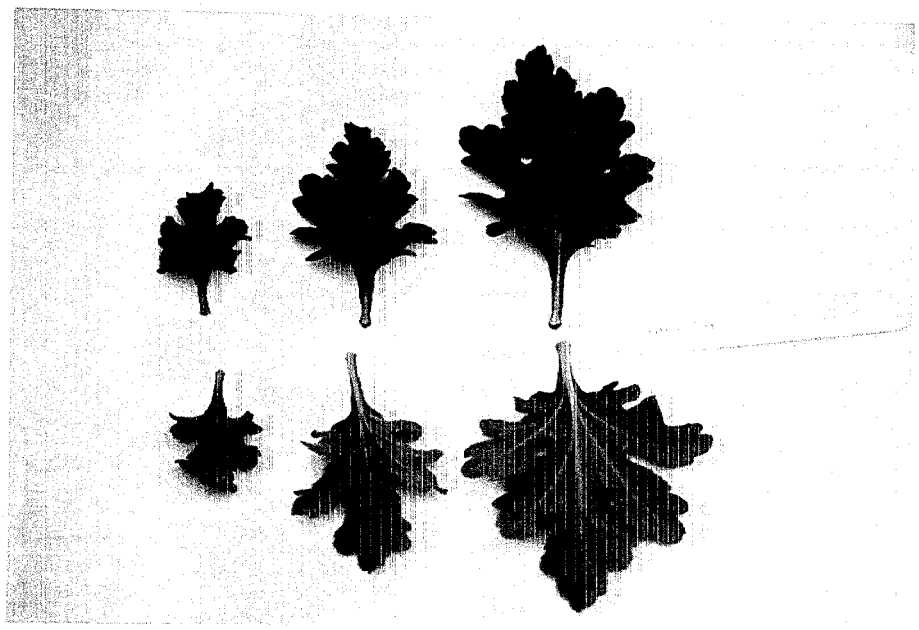
FIG. 3 illustrates at the top row the upper surfaces of typical leaves of various sizes and at the bottom row the under surfaces of typical leaves of various sizes.

The chart used in the identification of color described hereafter is the R.H.S. Colour Chart of the Royal Horticultural Society, London, England. In some instances more common color terms are provided and are to be accorded their usual dictionary significance. The plants described were 13 weeks of age and were grown at Nuaille, Trementines, France, under standard greenhouse conditions where approximate those commonly utilized for the production of decorative pot mums.

Classification:

*Botanical.*—*Dendranthema grandiflora,* cv. 'Chasica'.

*Commercial.*—Decorative pot mum.

Inflorescence

A. Capitulum:

*Form.*—Large, double, incurved.

*Type.*—Pompon.

*Diameter across face.*—Approximately 14 to 16 cm. on average when fully expanded.

B. Corolla of ray and disc florets:

*Color of bud.*—Greyed-Purple Group 185B.

*Disc florets.*—Tubular, yellow in coloration, few in number, very difficult to observe, and tend to be scattered among the ray florets with a small cluster at the apex of the receptacle that is visible only when the ray florets are removed. Such disc florets are classified as Type 2 pursuant to UPOV reference TG/26/4 of Nov. 14, 1979.

*General tonality.*—Deep red-bronze on the inside and golden-bronze on the outside. The blossom coloration generally is long lasting with some fading towards the brownish tones. Brighter coloration tends to occur during the natural flowering period.

*Color ray florets.*—Red Group 53A on the inside, and Greyed-Yellow Group 162A tinged with Greyed-Purple Group 185A between the ribs on the outside.

*Configuration ray florets.*—Incurved, concave in cross section, smooth, and possess pointed tips.

C. Reproductive organs:

*Androecium.*—Generally present with disc florets and absent in ray florets.

*Gynoecium.*—Generally present with most disc florets and with most ray florets.

*Pollen.*—Formed in a slight quantity and golden-yellow in coloration.

*Fragrance.*—Typical of Chrysanthemum.

Plant

A. General appearance:

*Height.*—Short, and approximately 45 cm. in height on average in the absence of a growth regulator. Height will vary somewhat depending upon growth conditions.

B. Foliage:

*Color (upper surface).*—Dark green, Green Group 137A.

*Color (under surface).*—Lighter green, approaches Green Group 138A.

*Long day leaf count.*—Approximately 31 to 35 leaves per typical stem in a long day crop before the bud occurs.

*Configuration.*—Lobed (as illustrated).

*Texture.*—Fleshy.

*Internode length.*—Very short.

*Stems.*—Thin to medium thickness, strong, angular in cross section, Yellow-Green Group 144A in coloration, and commonly with anthocyanin coloration at the nodes.

*Leaf claw in base of sinus between lateral lobes.*—Present.

*Leaf margins of sinus between lateral lobes.*—Converging.

*Leaf base.*—Asymmetric.

*Leaf apex.*—Cuspidate.

I claim:

1. A new and distinct cultivar of Chrysanthemum plant named 'Chasica', substantially as herein shown and described, which (a) exhibits attractive double very large incurved pompom blossoms that are deep red-bronze on the inside and golden-bronze on the outside.

(b) exhibits a flower response period of approximately nine and one-half weeks.

(c) forms attractive green foliage, (d) achieves a short plant height, and (e) is particularly suited for pot mum production on a recurrent basis throughout the year.

* * * * *